US006265592B1

(12) United States Patent
Birnbach et al.

(10) Patent No.: US 6,265,592 B1
(45) Date of Patent: Jul. 24, 2001

(54) METHOD FOR THE CONTINUOUS PRODUCTION OF 1,3-DIOXOLAN-2-ONES

(75) Inventors: Stefan Birnbach, Dirmstein; Toni Dockner, Meckenheim; Jürgen Mohr, Grünstadt; Regina Benfer, Altrip; Walter Bieg, Grünstadt; Jarren Peters, Mannheim; Bernd Ruge, Böohl-Iggelheim; Werner Weinle, Friedelsheim; Peter Zehner, Ludwigshafen, all of (DE)

(73) Assignee: BASF Aktiengesellschaft, Ludwigshafen (DE)

( * ) Notice: Subject to any disclaimer, the term of this patent is extended or adjusted under 35 U.S.C. 154(b) by 0 days.

(21) Appl. No.: 09/674,281

(22) PCT Filed: Apr. 22, 1999

(86) PCT No.: PCT/EP99/02701

§ 371 Date: Oct. 30, 2000

§ 102(e) Date: Oct. 30, 2000

(87) PCT Pub. No.: WO99/57108

PCT Pub. Date: Nov. 11, 1999

(30) Foreign Application Priority Data

Apr. 30, 1998 (DE) .............................................. 198 19 586

(51) Int. Cl.$^7$ ........................ C07D 317/68; C07D 317/12
(52) U.S. Cl. ........................................... 549/230; 549/229
(58) Field of Search ..................................... 549/229, 230

(56) References Cited

U.S. PATENT DOCUMENTS

| 2,773,881 | 12/1956 | Dunn | 260/340.2 |
| 4,892,954 | 1/1990 | Brindoepke et al. | 549/229 |

FOREIGN PATENT DOCUMENTS 35 29 263    2/1987   (DE) .

OTHER PUBLICATIONS

H. Matsuda, et al., Chemistry Letters, No. 12, pp. 1261–1262, "Reaction of Carbon Dioxide with Epoxides in the Presence of Pentavalent Organoantimony Compounds", 1979.

H. Koinuma, et al., Chemistry Letters, No. 5, pp. 517 to 520, "Synthesis of 1.2–Propanediol Formates from Carbon Dioxide, Hydrogen, and Methyloxirane Catalyzed by Transition Metal Comples", 1977.

*Primary Examiner*—Ba K. Trinh
(74) *Attorney, Agent, or Firm*—Oblon, Spivak, McClelland, Maier & Neustadt, P.C.

(57) ABSTRACT

A process for the continuous production of 1,3-dioxolan-2-ones such as ethylene carbonate or propylene carbonate by reacting a corresponding oxirane with carbon dioxide in the liquid phase in the presence of a catalyst comprises conducting the reaction in a two-part reactor in whose first part the reaction is taken with backmixing to a conversion of not less than 80% of the oxirane II and in whose second part the reaction is completed under nonbackmixing conditions, and passing the carbon dioxide in countercurrent to the oxirane II in the entire reactor.

16 Claims, No Drawings

METHOD FOR THE CONTINUOUS PRODUCTION OF 1,3-DIOXOLAN-2-ONES

This application is a 371 of PCT/EP 99/02701 dated Apr. 22, 1999.

The present invention relates to an improved process for continuous production of 1,3-dioxolan-2-ones such as ethylene carbonate or propylene carbonate from the corresponding oxiranes and carbon dioxide in the liquid phase in the presence of a catalyst.

In Ind. Eng. Chem. 50 (1958), 767–770, there is described a process for producing ethylene carbonate by reacting ethylene oxide with carbon dioxide in a tubular reactor whose top end is fed with ethylene oxide and catalyst solution at 155° C. and whose bottom end (at 195° C.) is fed with the carbon dioxide and discharges the ethylene carbonate produced. An after-reaction is carried out in a downstream, separate tank. The pressure in the reactor is 1500 psig (103 bar). It can be operated continuously. The carbon dioxide is offered in excess. Given the temperature gradient of 40° C. in the reactor, backmixing conditions are not present. A conversion of just below 99% is reached in the after-reactor, but a number of by-products are formed; the ethylene carbonate yield is thus about 93%.

It is an object of the present invention to provide an improved process which provides a particularly high conversion of the oxirane, in particular an oxirane conversion of not less than 99.9%, coupled with high selectivity and high space-time yield. Also, the product shall be so pure that by-products appear only in the ppm range. The desired high conversion is achieved in particular when a two-part reactor with countercurrent operation between oxirane and carbon dioxide is used for the purposes of the present invention.

We have found that this object is achieved by a process for continuous production of 1,3-dioxolan-2-ones of the general formula I

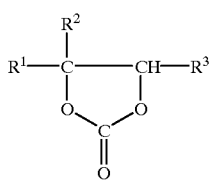

(I)

where $R^1$ is hydrogen or an organic radical having up to 40 carbon atoms and $R^2$ and $R^3$ are each hydrogen or $C_1$–$C_4$-alkyl, in which case $R^2$ and $R^3$ may also combine to form a five- or six-membered ring,
by reaction of an oxirane of the general formula II

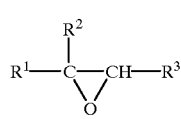

(II)

with carbon dioxide in the liquid phase in the presence of a catalyst, which comprises conducting the reaction in a two-part reactor in whose first part the reaction is taken with backmixing to a conversion of not less than 80%, especially not less than 90%, of the oxirane II and in whose second part the reaction is completed under nonbackmixing conditions, and passing the carbon dioxide in countercurrent to the oxirane II in the entire reactor.

Both parts of the reactor may each consist of a single stage or of a plurality of consecutive or parallel stages. The entire reactor may be constructed from one or more pieces of apparatus. Advantageously, the fresh oxirane II and the fresh catalyst are fed into the first part of the reactor and the fresh carbon dioxide is fed into the second part of the reactor.

It is important for the success of the process to ensure adequate backmixing within the first part of the reactor. The specific design of the first part of the reactor promotes backmixing or makes it possible in the first place, for example through the choice of a loop reactor. Furthermore, it is also possible and advantageous to use external backmixing systems, for example by pumping a portion of the product stream which leaves the first or second part of the reactor back into the first part.

The reaction in the first part of the reactor is advantageously carried out isothermally by removing the heat of reaction. Since the conversion of the oxiranes II to the 1,3-dioxolan-2-ones I is usually highly exothermic, effective heat removal is needed. In general, the heat of reaction is removed by an internal or external heat exchanger having a volume flow rate of from 30 to 500 times the throughput through the reactor. In general, the temperature fluctuations in the first part of the reactor do not exceed ±50° C., especially ±3° C.

The pressure under which the reactor is operated is normally within the range from 2 to 50 bar, especially within the range from 5 to 40 bar, in particular within the range from 10 to 30 bar, in both parts of the reactor. These relatively low pressures mean that the process of the invention is usually uncomplicated in terms of equipment requirements.

A further significant factor for the process of the invention to be economically successful is the maintenance of a certain temperature range within both parts of the reactor. The temperature should not exceed 150° C. in any part of the reactor. Preferred temperature ranges extend from 70 to 150° C., especially from 90 to 145° C., in particular from 100 to 140° C. The second part of the reactor may have a temperature which is up to 40° C., especially up to 25° C., in particular up to 10° C., above the temperature in the first part of the reactor.

A high conversion of not less than 80%, preferably not less than 90%, especially not less than 95%, in particular not less than 98%, in the first part of the reactor and the good backmixing in this part of the reactor generally ensure that oxirane concentrations do not exceed 20% by weight, preferably 10% by weight, especially 5% by weight, in particular 2% by weight, anywhere in the reactor. This not only has safety relevance (ethylene oxide!) but also has a significant bearing on the selectivity. It was found that an elevated oxirane concentration leads to increased by-product formation.

The first part of the reactor is preferably isothermal owing to a high adiabatic temperature increase. The heat of reaction can be removed by an internal or external heat exchanger, depending on the design of the reactor. The good backmixing in the reactor prevents the appearance of undesirable temperature spikes. Also, to support the reaction, it is advantageous for the gaseous carbon dioxide, which the invention has passing countercurrent to the oxirane II, to be finely dispersed in every part of the reactor in order that high mass transfer areas may be obtained. Normally, the carbon dioxide is present in a saturated state in the liquid phase. This ensures that sufficient carbon dioxide is available in the entire reactor. According to the present invention, a particularly advantageous way of carrying out the countercurrent procedure is for unconverted oxirane to be stripped from the second reactor part into the first part in which the main conversion takes place. This technique reduces the oxirane exit concentration in the alkylene carbonate produced and consequently promotes high conversion.

The reactor is generally built with the first, backmixed part as the upper part. The mixing in this part of the reactor is preferably obtained with a jet of liquid. To augment the mixing and gas absorption, the reactor may be fitted with internals, for example with a draft tube or a momentum transfer tube. The dispersing of the gas phase in this part of the reactor can take place via the jet of liquid or a finely divided supply of gas at the bottom. The catalyst and the fresh oxirane can be introduced at any desired point of this part of the reactor. Preference is given to introducing the oxirane in the jet of liquid, so that it comes to be present in the liquid in a state of uniform disbursement.

The catalyst passes with the liquid effluent from the first step into the second part of the reactor. The liquid effluent can leave the first part at any desired point, but preferably at the bottom. Inerts (noble gases, nitrogen) and unconverted carbon dioxide can be removed from the reaction mixture at the top of the reactor. A bleed stream of the off-gas can be returned to the second part of the reactor together with the fresh gas.

The second part of the reactor can be embodied as a multistage countercurrent gas and liquid contacting apparatus (operated with cooling or adiabatically). Preference is given to its embodiment as a bubble column battery, but other designs are also possible, for example a stirred tank battery. Division of this part of the reactor into a plurality of stages can be provided by internal fitments such as foraminous sheets, bubble cap trays or specific mixing elements or by using a plurality of pieces of apparatus. The gas should be dispersed as effectively as possible in every stage, for which appropriate static or dynamic gas dispersers such as foraminous sheets, nozzles or stirring elements are suitable. It is similarly possible to use a fixed bed with tubular reactor characteristics, consisting of packing elements or packed internals, possibly already with applied catalyst. In this case, the carbon dioxide is the stationary phase and the reaction solution forms a film on the internals, the result being again the creation of a large mass transfer area. It is also conceivable to add the fresh carbon dioxide gas split between the individual stages of the second part of the reactor. However, it is preferably all added in the last stage. To obtain a flow regime as explained above, it may be necessary to operate the two parts of the reactor and the individual stages at different pressure levels (within the framework of the range specified for the reactor as a whole). In this case, the last stage preferably has the highest pressure level.

The reaction mixture with product I of the process is continuously discharged from the last reactor stage.

Suitable catalysts for the process of the invention include virtually all catalysts known for such reactions from the literature, e.g., from U.S. Pat. Nos. 2,773,070, 2,773,881, Chem. Lett. (1979) p. 1261, Chem. Lett (1977) p. 517, DE-A 35 29 263, DE-B 11 69 459, EP-A 069 494 or EP-B 543 249. It is particularly advantageous, however, for onium salts or metal salts or mixtures thereof to be used as catalysts.

Suitable onium salts include in principle all compounds of this type, including in particular ammonium, phosphonium and sulfonium salts of the general formulae IIIa to IIIc

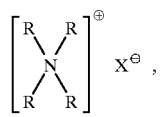

IIIa

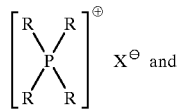

IIIb

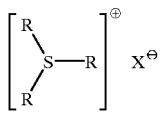

IIIc where the R substituents denote identical or different hydrocarbon radicals each having from 1 to 20 carbon atoms, subject to the proviso that the sum total of the carbon atoms in the R radicals should in each case not be greater than 24, and where X is in particular halogen, preferably bromine or iodine.

Owing to the general suitability of onium salts, their selection depends in the main on availability and cost. In practice, therefore, the choice will fall in particular on the ammonium salts IIIa, among which the commercially available and easily made tetraethylammonium bromide deserves pride of place. Emphasis must in addition be given to those compounds IIIa in which three of the R radicals are lower alkyl groups such as methyl or ethyl while the fourth is benzyl or an unbranched $C_6$- to $C_{18}$-alkyl radical.

Of the phosphonium salts IIIb, the best available are derived from triphenylphosphine and have a fourth substituent which was introduced into the molecule by quaternization with a $C_1$–$C_6$-alkyl bromide.

An example of a suitable sulfonium salt IIIa is the easily made trimethylsulfonium iodide. In general, however, the ammonium and phosphonium salts are more suitable than the sulfonium salts.

In general, hydrocarbyl R in the compounds IIIa to IIIc can be branched or preferably unbranched $C_1$–$C_{20}$-alkyl, aralkyl such as benzyl, cyclohexyl or aryl such as phenyl or p-tolyl. Furthermore, R alkyl radicals may also combine, for example to form a piperidine ring. Suitable anions apart from halogen include, for example, sulfate and nitrate.

Frequently, and specifically in the case of the onium bromides, it is not necessary to start from the salts IIIa to IIIc themselves; instead, it will be sufficient to use their precursor base and quaternizing reagent, which automatically give rise to the efficacious quaternization products IIIa to IIIc.

Suitable metal salts include salts of alkali metals, alkaline earth metals and transition metals, especially of divalent transition metals, for example sodium, potassium, magnesium, calcium, aluminum, manganese(II), iron(II), nickel(II), copper(II), zinc, cadmium or lead(II) salts. Suitable anions for these salts include sulfate, nitrate, phosphate, carbonate, acetate, formate and especially halides such as chloride, bromide and iodide. Particularly good results are obtained with zinc salts such as zinc sulfate, zinc nitrate, zinc phosphate, zinc carbonate, zinc acetate, zinc formate, zinc chloride, zinc bromide or zinc iodide. It will be readily understood that it is also possible to use mixtures of such metal salts, and this also applies to the abovementioned onium salts. Also, mixtures of onium salts with metal salts are possible and even show surprising advantages in some cases.

The amount of the onium salts and/or metal salts used as catalysts is in principle arbitrary, since it evidently merely influences the reaction rate, whose order of magnitude in turn depends on the type of oxirane II used. Industrially satisfactory reaction times from about 0.5 to 5 h generally require from about 0.01 to 3% by weight, based on oxirane II used.

In a preferred embodiment, the catalysts used are alkali metal bromides, alkali metal iodides, tetraalkylammonium bromides, tetraalkylammionium iodides, halides of divalent metals or mixtures thereof.

In a very particularly preferred embodiment, the catalyst used is a mixture of onium salts, especially ammonium, phosphonium and/or sulfonium salts of the general formula IIIa to IIIc, and zinc salts, especially those explicitly mentioned above. The effective amount of zinc salt here varies with the reactivity of the oxirane used, the activity of the onium salt and the other reaction conditions from 0.1 to 1.0 mol, preferably from 0.3 to 0.7 mol, per mole of onium salt. When zinc bromide is used, these amounts generally range from 0.2 to 0.8 mol, preferably from 0.3 to 0.5 mol, pro mole of onium salt.

The process of the invention can be carried out without solvent, but an inert solvent such as dioxane, toluene or acetone can be used, normally in amounts from about 10 to 100% by weight, based on oxirane II used. If product I is liquid under the reaction conditions, it is advantageously used as solvent. In such cases, it will be advantageous to dissolve the catalyst in the product and to meter this solution into the reactor, which practically contains no further solvents. In this embodiment, the concentration of catalyst in product I is customarily in the 30 range from 0.5 to 20% by weight, especially within the range from 1 to 15% by weight; the molar ratio of the amount of reactant II added over the same unit time to product I added with the catalyst is generally within the range from 100:1 to 1:1, especially within the range from 50:1 to 2:1.

In the process of the invention, the reactant streams of oxirane II and carbon dioxide are preferably used in a molar ratio of from 1:1 to 1:1.05, especially in a molar ratio of from 1:1 to 1:1.02. A possible small excess of carbon dioxide is necessitated by the losses of carbon dioxide during decompression.

The process of the invention normally provides virtually quantitative conversions of II, generally of not less than 99%, especially not less than 99.5%, in particular not less than 99.9%, whereupon the reaction mixture is in principle worked up in a conventional manner. The catalyst-comprising residues obtained can usually be used repeatedly for further reaction batches until any metal salt used has been deactivated by hydrolysis due to the unavoidable presence of traces of water.

For a very pure product to be obtained, given a suitable combination of reaction conditions and catalyst type and concentration, generally only requires removal of catalyst and of unconverted oxirane. Catalyst removal and recycle is also advisable from economic aspects. The product can be worked up in several ways. In general, it is first necessary to remove the dissolved carbon dioxide by decompression. Customary unit operations such as distillation, extraction or stripping can be used both for catalyst removal and for oxirane removal.

According to observations to date, successful performance of the process of the invention is not dependent on the type of oxirane (epoxide) II used, provided the radical $R^1$ (as should be self-evident) does not contain any acidic substituents which give rise to secondary reactions by opening the oxirane ring.

Suitable $R^1$ radicals besides hydrogen include:

saturated and unsaturated branched and unbranched aliphatic radicals having up to 40 carbon atoms, especially up to 18 carbon atoms, iso- or heterocyclic cycloaliphatic groups having preferably from 5 to 7 ring members, iso- or heterocyclic aromatic groups, and mixed radicals containing groups of the aforementioned kind, for example araliphatic radicals such as benzyl.

The group may bear substituents such as halogen, nitro groups, free or substituted amino groups, hydroxyl groups, formyl groups or cyano groups or contain ether, ketone or ester groups.

$R^2$ and $R^3$ are each generally hydrogen, methyl or radicals which combine to form a five- or six-membered ring, an example of which is cyclohexene oxide as compound II. If II contains two oxirane rings each having one $CH_2$-group, the corresponding bisdioxolanes I are obtained. Oxirane rings substituted on both carbon atoms are generally less susceptible to attack than those which are only substituted on one of the carbon atoms.

A preferred embodiment of the process of the invention comprises producing 1,3-dioxolan-2-ones of the general formula I where $R^1$ is hydrogen or $C_1$–$C_{18}$-alkyl, especially $C_1$–$C_4$-alkyl. The process of the invention is very particularly useful for producing ethylene carbonate or propylene carbonate, but also for producing the carbonates of isobutylene oxide, styrene oxide or epichlorohydrin.

Products I of the process are useful intermediates for organic syntheses. In addition, ethylene carbonate and propylene carbonate are widely used as solvents, especially in the synthetic fiber industry.

EXAMPLE 1

Preparation of Propylene Carbonate

The reactor used comprised a first (upper) part (a loop reactor) having an external recirculation system with an external heat exchanger, via which the reaction temperature was maintained at 120° C.±2° C., and a second (lower) part consisting of a five-stage countercurrent bubble column battery operating at temperatures from 122° C. (in the uppermost stage) to 130° C. (in the lowest stage). The reactor was operated at a pressure of 16 bar in all parts.

The upper part of the reactor was continuously fed with 2.00 kg/h of propylene oxide and also 0.456 kg/h of a solution of 12% by weight of a zinc bromide/tetraethylammonium bromide mixture in a weight ratio of 1:2 as catalyst dissolved in propylene carbonate. The bottom of the lowest stage of the bubble column battery was continuously fed with 1.52 kg/h of carbon dioxide and at the same time continuously discharged 4.00 kg/h of product. The discharged propylene carbonate included in solution a propylene oxide content of only about 200 ppm; by-products such as acetone and propionaldehyde were present in a concentration of considerably less than 200 ppm. The conversion was 99.9%, based on propylene oxide used.

EXAMPLE 2

Preparation of Ethylene Carbonate

The same reactor and the same reaction parameters as in Example 1 were used.

The upper reactor stage was continuously fed with 1.52 kg/h of ethylene oxide and also 0.27 kg/h of a solution of 12% by weight of a zinc bromide/tetraethylammonium bromide mixture in a weight ratio of 1:2 as catalyst dissolved in ethylene carbonate. The bottom of the lowest stage of the bubble column battery was continuously fed with 1.52 kg/h of carbon dioxide and at the same time continuously discharged 3.30 kg/h of product. The discharged ethylene carbonate had an ethylene oxide content of less than 100 ppm; by-products such as acetaldehyde were present in a concentration of only about 10 ppm. The conversion was 99.95%, based on ethylene oxide used.

We claim:

1. A process for continuous production of 1,3-dioxolan-2-ones of the general formula I

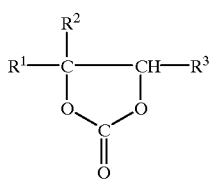

(I)

where $R^1$ is hydrogen or an organic radical having up to 40 carbon atoms and $R^2$ and $R^3$ are each hydrogen or $C_1$–$C_4$-alkyl, in which case $R^2$ and $R^3$ may also combine to form a five- or six-membered ring,
by reaction of an oxirane of the general formula II

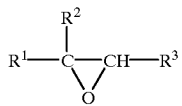

(II)

with carbon dioxide in the liquid phase in the presence of a catalyst, which comprises conducting the reaction in a two-part reactor in whose first part the reaction is taken with backmixing to a conversion of not less than 80%, of the oxirane II and in whose second part the reaction is completed under nonbackmixing conditions, and passing the carbon dioxide in countercurrent to the oxirane II in the entire reactor.

2. The process as claimed in claim 1, wherein the fresh oxirane II and the fresh catalyst are fed into the first part of the reactor and the fresh carbon dioxide is fed into the second part of the reactor.

3. The process according to claim 1, wherein the reaction in the first part of the reactor is carried out isothermally by removing the heat of reaction.

4. The process as claimed in claim 3, wherein the heat of reaction is removed by an internal or external heat exchanger having a volume flow rate of from 30 to 500 times the throughput through the reactor.

5. Then process as claimed in claim 1, wherein the reaction is completed up to a conversion of not less than 99% of the oxirane II in the second part of the reactor.

6. The process as claimed in claim 1, wherein the reactor is operated at from 2 to 50 bar in both parts.

7. The process as claimed in claim 1, wherein the reactor is operated at from 70 to 150° C. in both parts.

8. The process as claimed in claim 1, wherein the oxirane II and the carbon dioxide are used in a molar ratio of from 1:1 to 1:1.05.

9. The process as claimed in claim 1, wherein the catalysts used are onium salts or metal salts or mixtures thereof.

10. The process as claimed in claim 9, wherein the catalysts used are selected from the group consisting of alkali metal iodides, alkali metal bromides, tetraalkylammonium iodides, tetraalkylammonium bromides, halides of divalent metals and mixtures thereof.

11. The process as claimed in claim 1 for producing the 1,3-dioxolan-2-ones I where $R^1$ is hydrogen or $C_1$–$C_8$-alkyl.

12. The process as claimed in claim 11 for producing ethylene carbonate or propylene carbonate.

13. A process as claimed in claim 1, wherein the reaction is taken with backmixing to a conversion of not less than 90%.

14. A process as claimed in claim 5, wherein the reaction is completed up to a conversion of not less than 99.5%.

15. A process as claimed in claim 6, wherein the reactor is operated at from 5 to 40 bar.

16. A process as claimed in claim 7, wherein the reactor is operated at from 90 to 145° C.

* * * * *